US011623022B2

(12) United States Patent
Marra et al.

(10) Patent No.: US 11,623,022 B2
(45) Date of Patent: Apr. 11, 2023

(54) SYSTEMS AND METHODS FOR RECONSTRUCTION OF NERVE DEFECTS

(71) Applicant: UNIVERSITY OF PITTSBURGH—OF THE COMMONWEALTH SYSTEM OF HIGHER EDUCATION, Pittsburgh, PA (US)

(72) Inventors: Kacey Gribbin Marra, Canonsburg, PA (US); Jacqueline Wittmer, Allison Park, PA (US)

(73) Assignee: University of Pittsburgh—of the Commonwealth System of Higher Education, Pittsburgh, PA (US)

(*) Notice: Subject to any disclaimer, the term of this patent is extended or adjusted under 35 U.S.C. 154(b) by 117 days.

(21) Appl. No.: 16/763,753

(22) PCT Filed: Nov. 13, 2018

(86) PCT No.: PCT/US2018/060788
§ 371 (c)(1),
(2) Date: May 13, 2020

(87) PCT Pub. No.: WO2019/099394
PCT Pub. Date: May 23, 2019

(65) Prior Publication Data
US 2020/0368390 A1   Nov. 26, 2020

Related U.S. Application Data

(60) Provisional application No. 62/586,543, filed on Nov. 15, 2017.

(51) Int. Cl.
*A61L 27/36* (2006.01)
*A61L 27/18* (2006.01)
(Continued)

(52) U.S. Cl.
CPC .......... *A61L 27/3604* (2013.01); *A61L 27/18* (2013.01); *A61L 27/54* (2013.01); *A61L 27/58* (2013.01);
(Continued)

(58) Field of Classification Search
None
See application file for complete search history.

(56) References Cited

U.S. PATENT DOCUMENTS 6,972,168 B2    12/2005  Muir
9,498,221 B2 *  11/2016  Kokai ............... A61K 9/50
(Continued)

FOREIGN PATENT DOCUMENTS

WO   WO-2013066619 A1 *  5/2013  ......... A61B 17/1128

OTHER PUBLICATIONS

Ducic et al. Innovative Treatment of Peripheral Nerve Injuries: Combined Reconstructive Concepts, Annals of Plastic Surgery, Feb. 2012, vol. 68, No. 2, pp. 180-187. (Year: 2012).*

(Continued)

*Primary Examiner* — Carlos A Azpuru
*Assistant Examiner* — Casey S Hagopian
(74) *Attorney, Agent, or Firm* — Baker Botts L.L.P.

(57) ABSTRACT

Composite nerve guides for nerve regeneration are provided, wherein the composite guide comprise a nerve graft and a nerve conduit continuing an active agent that promote axon regeneration. The devices can provide structural supports to guide nerve regeneration and locally deliver an active agent (e.g., glial cell-line derived neurotrophic factor (GDNF) and/or glial growth factor 2 (GGF2) to injured nervous system tissue upon implantation in a subject. Methods of treatment using such devices are also provided.

22 Claims, 11 Drawing Sheets

(51) Int. Cl.
*A61L 27/54* (2006.01)
*A61L 27/58* (2006.01)

(52) U.S. Cl.
CPC ............... *A61L 2300/414* (2013.01); *A61L 2300/606* (2013.01); *A61L 2300/622* (2013.01); *A61L 2420/02* (2013.01); *A61L 2430/32* (2013.01)

(56) References Cited

U.S. PATENT DOCUMENTS

| | | | | |
|---|---|---|---|---|
| 9,750,851 B2* | 9/2017 | Kokai | ........................ | A61K 9/50 |
| 2013/0190687 A1* | 7/2013 | Kokai | ........................ | A61K 9/50 604/93.01 |

OTHER PUBLICATIONS

Bloch et al., "Nerve growth factor- and neurotrophin-3-releasing guidance channels promote regeneration of the transected rat dorsal root," Exp Neurol 172:425-432 (2001).
Chen et al., "Gelatin-tricalcium phosphate membranes immobilized with NGF, BDNF, or IGF-1 for peripheral nerve repair: an in vitro and in vivo study," J Biomed Mater Res A 846-857 (2006).
Di Scipio et al., "A simple protocol for paraffin embedded myelin sheath staining with osmium tetroxide for light microscope observation," Microsc Res Tech 71:497-502 (2008).
Dodia et al., "Differences between the effect of anisotropic and isotropic laminin and nerve growth factor presenting scaffolds on nerve regeneration across long peripheral nerve gaps," Biomaterials 29:33-46 (2008).
Fine et al., "GDNF and NGF released by synthetic guidance channels support sciatic nerve regeneration across a long gap," Eur J Neurosci 15:589-601 (2002).
Goraltchouk et al., "Incorporation of protein-eluting microspheres into biodegradable nerve guidance channels for controlled release," J Control Release 110:400-407 (2006).
International Search Report dated Feb. 7, 2019 in International Application No. PCT/US2018/060788.
Jiang et al., "Intravitreal injections of GDNF-loaded biodegradable microspheres are neuroprotective in a rat model of glaucoma," Mol Vis 13:1783-1792 (2007).
Kim et al., "Nerve injuries: operative results from major nerve injuries, entrapments, and tumors," 2nd ed. Philadelphia: Saunders Elsevier pp. 1-611 (2008).
Kokai et al., "Diffusion of soluble factors through degradable polymer nerve guides: controlling manufacturing parameters," Acta Biomater 5:2540-2550 (2009).
Lee et al., "Controlled release of nerve growth factor enhances sciatic nerve regeneration," Exp Neurol 184:295-303 (2003).
Lewin et al., "Simultaneous treatment with BDNF and CNTF after peripheral nerve transection and repair enhances rate of functional recovery compared with BDNF treatment alone," Laryngoscope 107 992-999 (1997).
Newman et al., "Ciliary neurotrophic factors enhances peripheral nerve regeneration," Arch Otolaryngol Head Neck Surg 22 399-403 (1996).
Rosner et al., "Rational design of contact guiding, neurotrophic matrices for peripheral nerve regeneration," Ann Biomed Eng 31 1383-1401 (2003).
Schlosshauer et al. "Synthetic nerve guide implants in humans: a comprehensive survey," Neurosurgery 59 740-748 (2006).
Singh et al., "Microsphere-based seamless scaffolds containing macroscopic gradients of encapsulated factors for tissue engineering," Tissue Eng Part C Methods 14(4):299-309 (2008).
Taylor et al., "The Incidence of Peripheral Nerve Injury in Extremity Trauma," Am J Phys Med Rehabil 87(5): 381-385 (2008).
Vasudevan et al., "Detergent-free Decellularized Nerve Grafts for Long-gap Peripheral Nerve Reconstruction," Plast Reconstr Surg Glob Open 2 e201 (2014).
Willerth et al., "Approaches to neural tissue engineering using scaffolds for drug delivery," Adv Drug Deliv Rev 59 325-38 (2007).
Wood et al., "Controlled release of glial-derived neurotrophic factor from fibrin matrices containing an affinity-based delivery system," J Biomed Mater Res A 89A(4):909-918 (2009).
Xu et al., "Peripheral nerve regeneration with sustained release of poly(phosphoester) microencapsulated nerve growth factor within nerve guide conduits," Biomaterials 24 2405-12 (2003).

* cited by examiner

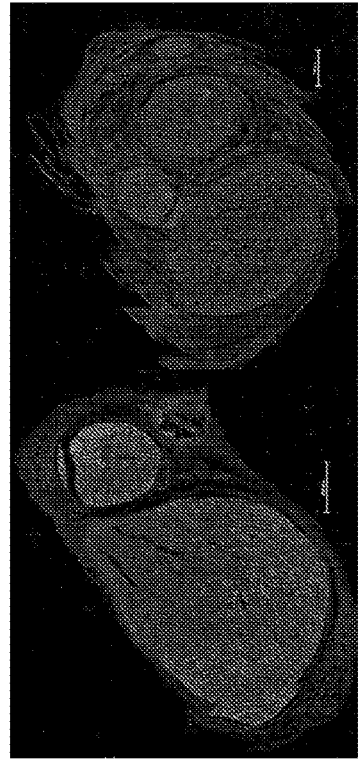
Figure 9C
Figure 9D
Figure 9E

SYSTEMS AND METHODS FOR RECONSTRUCTION OF NERVE DEFECTS

1. CROSS-REFERENCE TO RELATED APPLICATIONS

This application is a U.S. National Stage Patent Application under 35 U.S.C. § 371 of International Application No. PCT/US2018/060788, filed on Nov. 13, 2018, which claims priority to U.S. Provisional Application Ser. No. 62/586,543, filed Nov. 15, 2017, the contents of which are incorporated by reference herein in their entireties.

2. GRANT INFORMATION

This invention was made with government support under grants W81-WH-08-2-0032 and W81-WH-14-2-0003 awarded by the Department of Defense. The government has certain rights in the invention.

3. FIELD

The present invention relates to a composite guide that includes a nerve allograft and a nerve conduit. Said composite guide may be used to reconstruct nerve defects and/or promote nerve regeneration by delivering one or more active agents such as nerve growth factors.

4. BACKGROUND OF THE INVENTION

Certain nerve related injuries can be caused by trauma, bone fracture, joint dislocation, tumor removal, and accidental surgical resection. [1] The current clinical "gold standard" for treating peripheral nerve injuries involves excising a portion of a non-essential sensory nerve to create an autograft, and subsequently transplanting this autograft into a gap in the injured nerve. [2] However, autografts can pose significant disadvantages for patients. [3] For example, nerve autografts can be associated with loss of sensation as well as formation of neuromas at the donor site, and lengthen the patient's time in the operating room, all of which negatively impact patient outcome. Surgeons are also limited in the number and diameter of nerves that they can harvest. This can complicate trauma situations in which multiple peripheral nerve injuries are sustained.

When an autograft is not possible or desirable, certain nerve guides can be used to reconstruct defects. In addition to providing mechanical support for regenerating nerves, nerve guides can provide cues that guide axonal growth and increase the rate at which nerves regenerate. [4] However, no commercially available nerve guide is currently approved to repair long gap peripheral nerve defects (i.e. gaps greater than 3 cm). While an autograft can in principle be used to bridge long gap peripheral nerve defects, the commercially available nerve guides have not equaled the regenerative capacity of the nerve autograft in long gap peripheral nerve defects.

For these reasons, a number of alternative approaches have been suggested. In particular, several studies have shown beneficial effects of delivering active agents (e.g., ciliary neurotrophic factor and glial cell line-derived neurotrophic) to the injured nerve's defected area. [5-11] Because of promising reports following treatment of nerve injuries with neurotrophic factors, several strategies have been developed for protein delivery from polymer nerve guides. [12-17] Due to limitations in the fabrication process and a lack of a mechanism that actively accelerates the nerve regeneration process through the controlled secretion of growth factors, however, certain conduit delivery systems release insufficient growth factors to promote the amount of nerve regeneration required, for example, to bridge long gap peripheral nerve defects.

Accordingly, there remains a need in the art for improved nerve guides that can deliver an active agent for reconstruction of nerve defects.

5. SUMMARY OF THE INVENTION

The present invention relates to a composite nerve guide comprising a combination of a nerve conduit and a nerve graft to achieve enhanced regeneration of nerves in long gap nerve defects. The present invention can provide similar length of structural support for nerve extensions, as compared to allograft, and deliver an active agent to local nervous system tissue to promote enhanced nerve growth and/or neurodegeneration.

In certain aspects, a composite nerve guide for promoting growth or reconstruction of a nerve can include an outer nerve conduit and an inner nerve graft. In certain non-limiting embodiments, the outer nerve conduit can comprise a polymer tube having a lumen including an inner layer comprising a biodegradable polymer, and an outer layer comprising a biodegradable polymer. For example, the biodegradable polymer can comprise poly(caprolactone), poly(lactide), and/or poly(lactic-co-glycolic acid). The outer layer can encapsulate the inner layer.

In some embodiments, the inner layer of the nerve conduit can include double-walled microspheres. The double-walled microspheres can comprise a biodegradable polymer. For example, a poly(lactic-co-glycolic acid) layer forms a core and a poly(lactide) layer forms a shell of the double-walled microsphere. In certain non-limiting embodiments, the microspheres can provide sustained release of the active agent in an amount effective in promoting nerve regeneration. For example, but not by way of limitation, the microspheres can release glial cell-line derived neurotrophic factor (GDNF) or glial growth factor 2 (GGF2) over at least seven days in an amount effective in promoting nerve regeneration.

In further aspects, the inner nerve graft can comprise an acellular nerve graft. The nerve graft can be decellularized by one or a combination of treatments including gamma irradiation, mechanical and chemical decellularization (detergent-processing), and a combination of these techniques. As a non-limiting example, the inner nerve graft can include a decellularized allograft, autograft, or xenograft.

In certain other aspects, the present invention relates to methods for promoting nerve growth or regeneration. The method can include implanting a composite nerve guide into a gap in an injured nerve, for example, but not limited to, a nerve gap longer than 3 cm.

6. BRIEF DESCRIPTION OF THE FIGURES

Figure 5B:
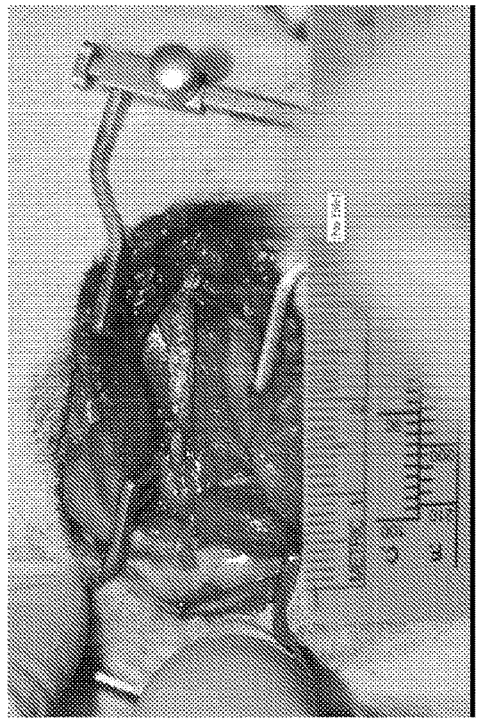
Figure 5D:
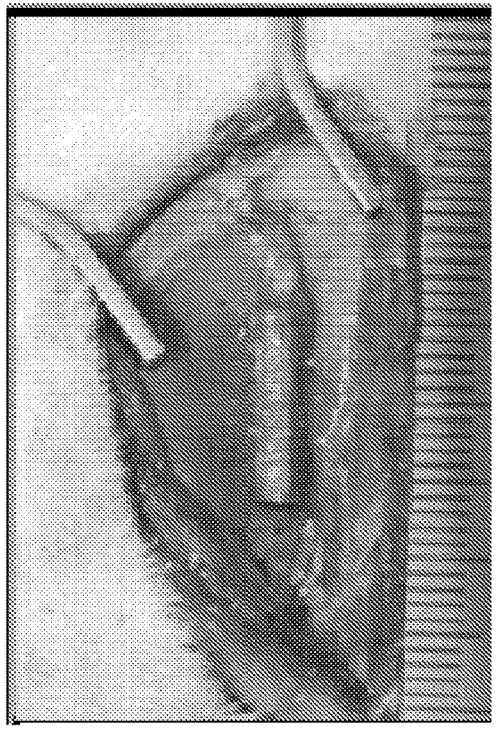
Figure 5A:
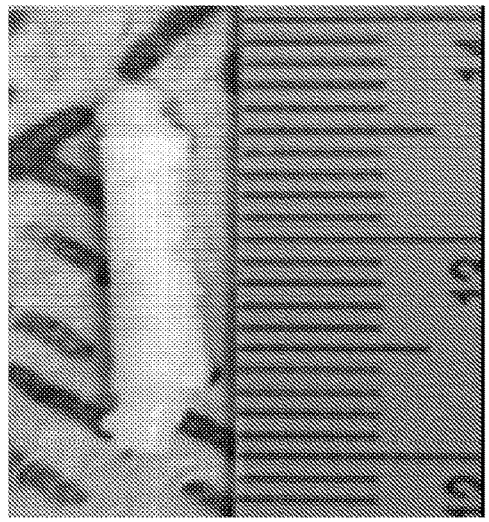
Figure 5C:
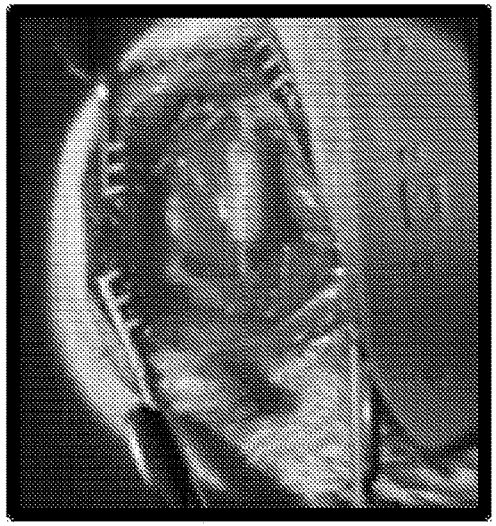

FIG. 5A provides a photograph of the nerve guide including an inner decellularized nerve allograft structure and outer nerve conduit for glial-cell line derived neurotrophic factor (GDNF) drug delivery into the graft. FIG. 5B illustrates a photograph of 1.5 cm critical sized defect on the sciatic nerve of rat implanted with an exemplary nerve guide. FIG. 5C provides a photograph of the nerve guide implanted into sciatic nerve of rat at time of implantation. FIG. 5D illustrates a photograph of the nerve guide 6 weeks after implantation into a sciatic nerve of rat.

Figure 6B:
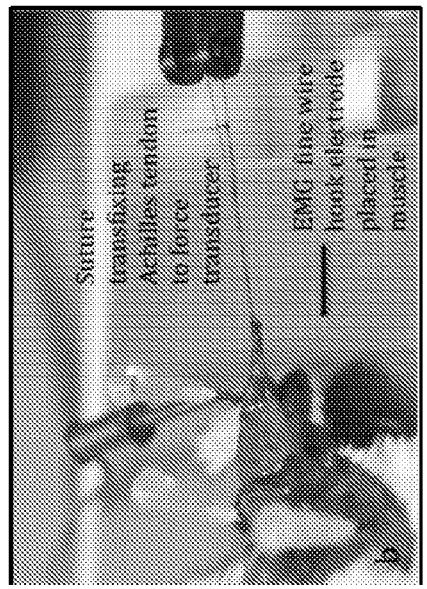
Figure 6A:
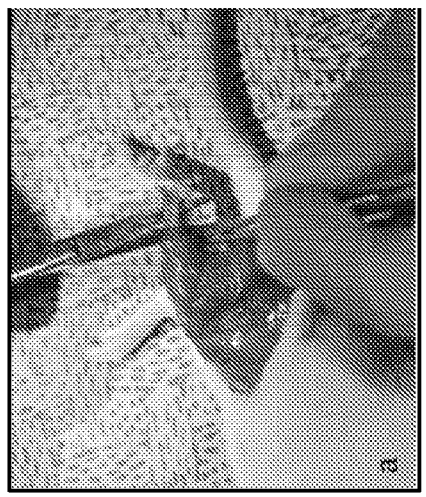

FIG. 6A is a photograph showing the achilles tendon and gastrocnemius muscle of rat leg. FIG. 6B is a photograph illustrating a force transducer and EMG set-up for stabilization of ret leg.

Figure 7A:
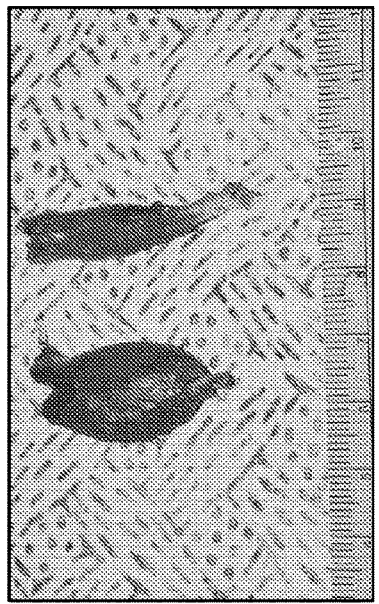
Figure 7B:
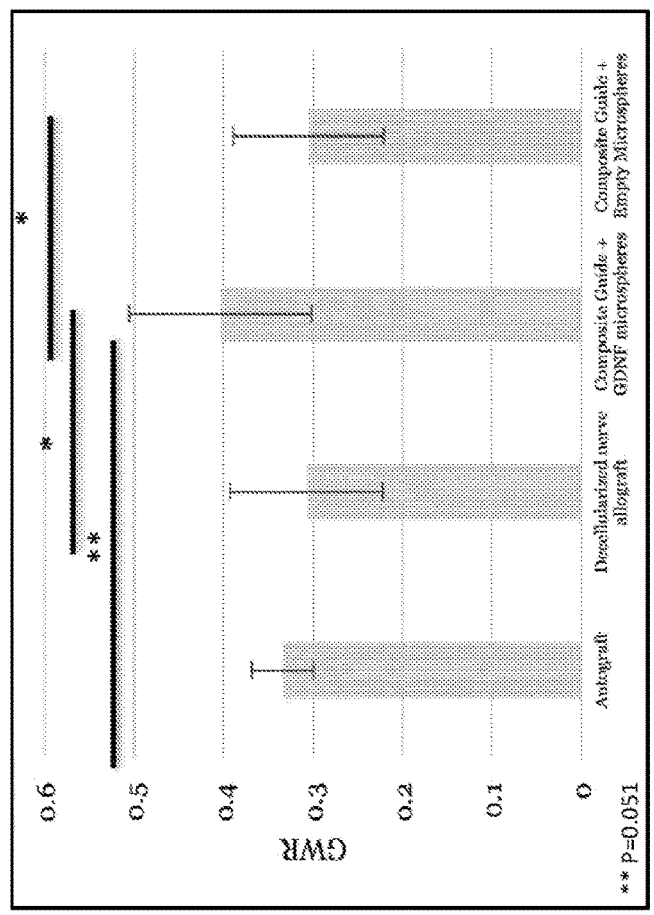

FIG. 7A provides a photograph of isolated (left) native gastrocnemius muscle and (right) treated muscle with an exemplary nerve guide from the achilles tendon and soleus muscle. FIG. 7B is a graph depicting the gastrocnemius muscle weight ratio (GWR) between treatment groups (an autograft, a decellularized nerve allograft, a PCL/GDNF conduit with a decellularized nerve allograft, and a nerve guide containing empty microspheres) at 6 weeks postoperatively. GWR is the weight of the operated gastrocnemius muscle normalized to naïve gastrocnemius muscle weight.

Figure 8:
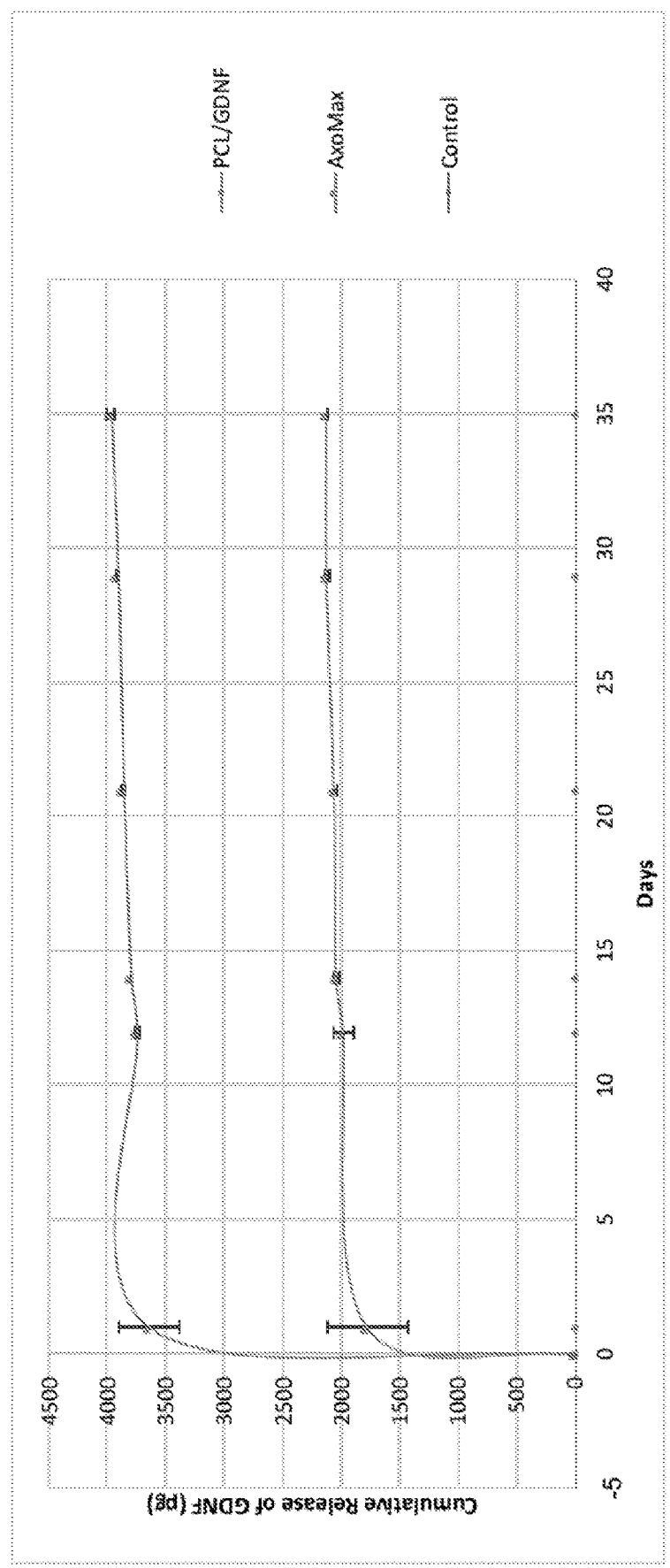

FIG. 8 is a graph depicting cumulative GDNF release from an exemplary PCL/GDNF conduit, an exemplary PCL/GDNF conduit with a decellularized nerve allograft, and an exemplary empty composite guide.

FIGS. 9A-E provide fluorescent microscopy images demonstrating Neurofilament and Schwann cells of rat sciatic nerves. The proximal nerve is on the left, and the distal nerve is on right. Neurofilament and Schwann cells of (A) Native nerve, (B) Autograft, (C) Composite guide with microspheres, (D) Decellularized nerve allograft, and (E) Empty composite guide are illustrated.

Figure 10B:
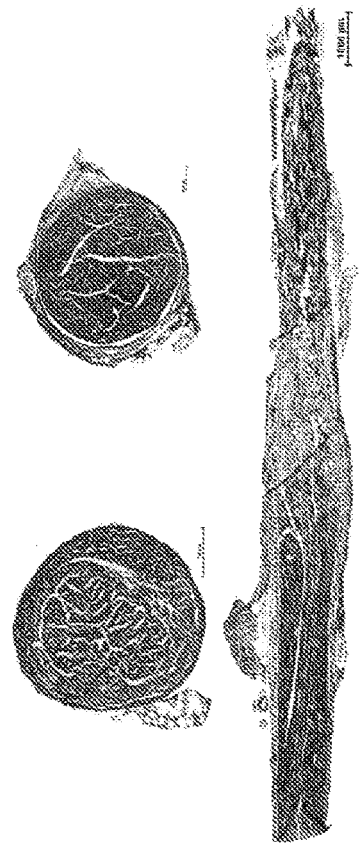
Figure 10D:
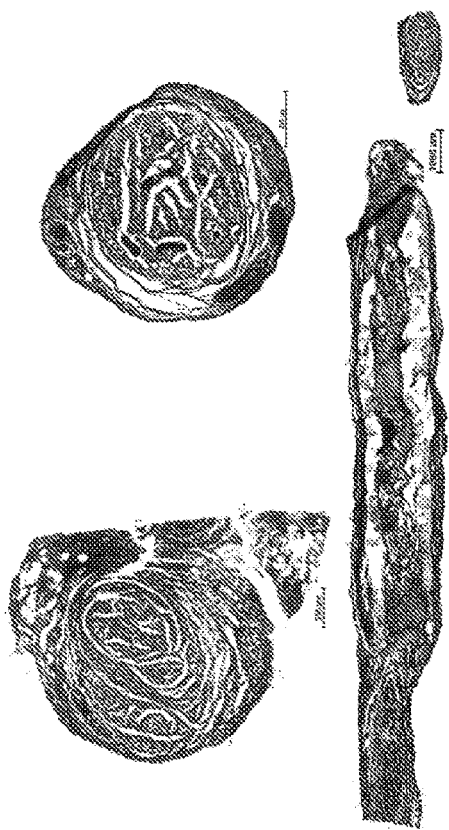
Figure 10A:
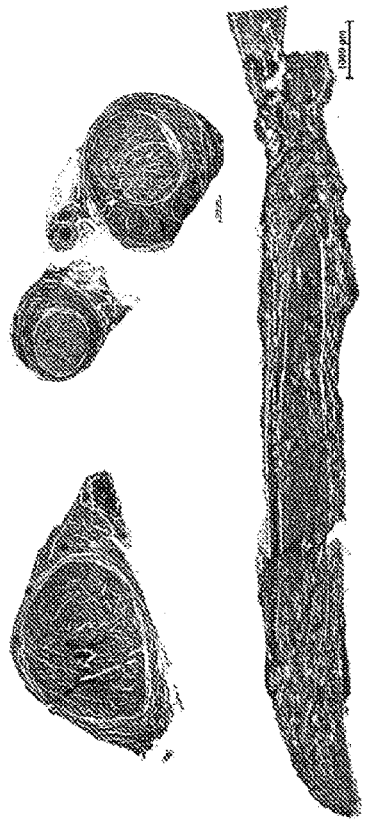
Figure 10C:
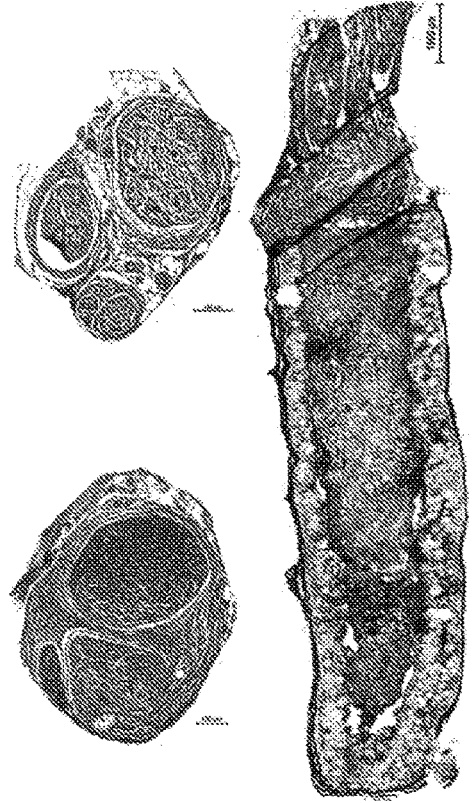

FIGS. 10A-D are compilation of brightfield micrographs taken of a transverse section of the rat sciatic nerves visualized with Masson's trichrome stain. In each group of sections, the top left is a proximal cross-section, top right is a distal cross-section, and a longitudinal section is on the bottom. FIG. 10A depicts rat sciatic nerves treated with reverse polarity autograft. FIG. 10B depicts rat sciatic nerves treated with decellularized nerve allograft. FIG. 10C depicts rat sciatic nerves treated with nerve guide with containing empty microspheres. FIG. 10D depicts rat sciatic nerves treated with composite guide with microspheres.

7. DETAILED DESCRIPTION OF THE INVENTION

The present invention relates to a composite guide that is based on a combination of a nerve conduit and a nerve graft to achieve an extension of nerves in long gap nerve defects. The present invention can provide mechanical and structural supports to guide axon extensions. Furthermore, the present invention can deliver an active agent to nervous system tissue, for example a damaged nerve, and can thereby be used to promote nerve growth and/or neurodegeneration.

For clarity of description, and not by way of limitation, the detailed description of the invention is divided into the following subsections:

(1) Definitions;
(2) Device for regeneration of nerve defects;
(3) Methods of making such devices; and
(4) Methods of treatment.

7.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the systems and methods of the invention and how to make and use them.

As used herein, the use of the word "a" or "an" when used in conjunction with the term "comprising" in the claims and/or the specification can mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "allograft" refers to a tissue graft from a donor of the same species as the recipient but genetically identical. For example, but not by limitation, the allograft tissue can include bone, bone marrow, kidney, liver, lung, corneal, pancreas, intestine, blood, uterus, thymus, ovary, tendons, ligaments, skin and heart valves.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of", and "consisting essentially of," the embodiments or elements presented herein, whether explicitly set forth or not.

The term "decellularized organ" as used herein refers to an organ, or part of an organ from which the entire cellular and tissue content has been removed leaving behind a complex interstitial structure. Organs are composed of various specialized tissues. The specialized tissue structures of an organ are the parenchyma tissue, and they provide the specific function associated with the organ. Most organs also have a framework composed of unspecialized connective tissue which supports the parenchyma tissue. The process of decellularization removes the parenchyma tissue, leaving behind the three-dimensional interstitial structure of connective tissue, primarily composed of collagen. The interstitial structure has the same shape and size as the native organ, providing the supportive framework that allows cells to attach to, and grow on it. Decellularized organs can be rigid, or semi-rigid, having an ability to alter their shapes. Examples of decellularized organs include, but are not limited to the heart, nerve, kidney, liver, pancreas, spleen, bladder, ureter and urethra.

As used herein, an "effective amount" refers to an amount of the active agent, e.g., Glial Cell Line-Derived Neurotrophic Factor (GDNF) that is able to facilitate regeneration of neurons. An "effective amount" may depend upon the context in which it is being applied, and can be based on several factors, including the condition and/or degree of injury of the neurons, the area being treated, and the duration of the treatment.

As used herein, a "protein" or "polypeptide" refers to a molecule comprising at least one amino acid residue.

A "subject" herein may be a human or a non-human animal, for example, but not by limitation, rodents such as mice, rats, hamsters, and guinea pigs; rabbits; dogs; cats; sheep; pigs; goats; cattle; horses; and non-human primates such as apes and monkeys, etc.

7.2 Device for Regeneration of Nerve Defects

Figure 1:
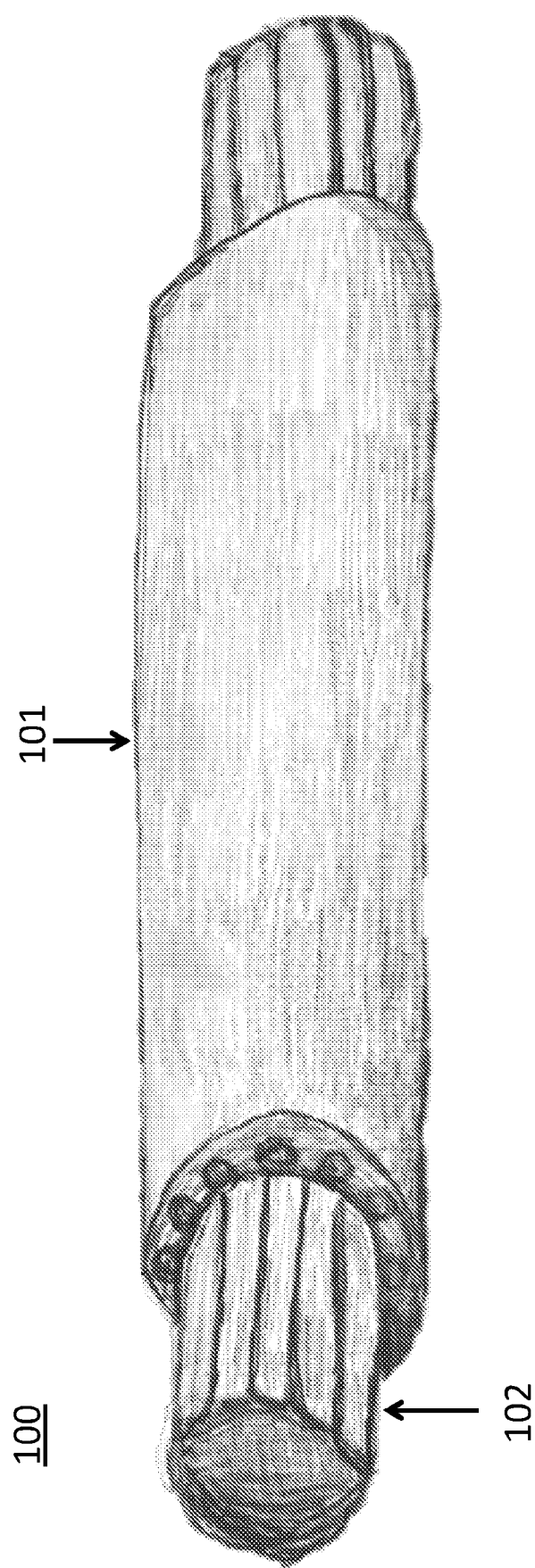
FIG. 1 is a schematic side view of the nerve guide in accordance with certain non-limiting embodiments of the present invention.
Figure 2:
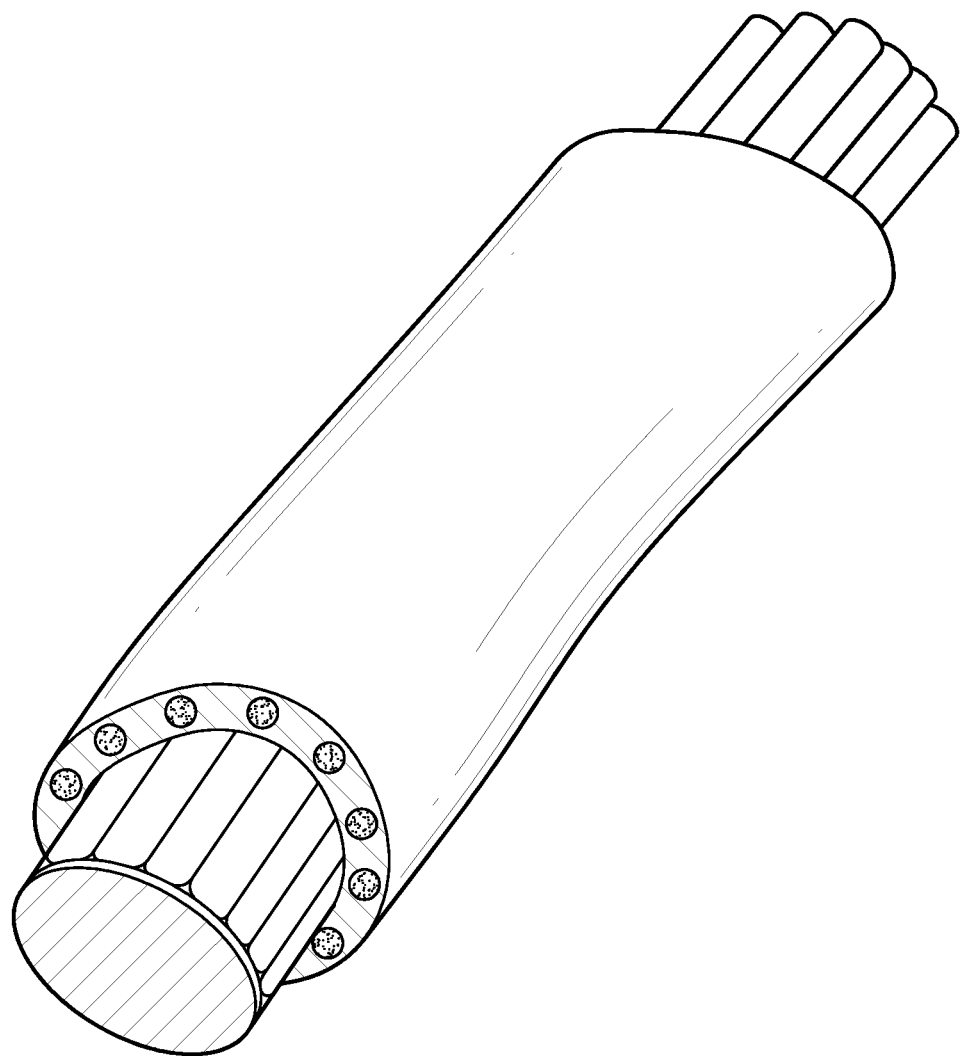
FIG. 2 is a schematic full view of the nerve guide in accordance with certain non-limiting embodiments of the present invention.

In certain aspects, the present invention provides a composite nerve guide that can comprise an inner nerve graft and an outer nerve conduit. The inner nerve graft can be used to bridge severed nerves and to provide structural support for regenerating nerves. The outer nerve conduit can locally deliver an active agent in physiologically relevant concentrations for pre-selected periods. The outer nerve conduit partially, substantially, or completely covers the inner nerve graft, although the invention contemplates that there may be one or more of empty space or a third element, together with the nerve graft, internal to the outer nerve conduit. In non-limiting embodiments, as shown in FIGS. 1 and 2, the outer nerve conduit 101 can surround the inner nerve graft 102 to enhance the nerve regeneration that can be seen with decellularized nerve allograft alone.

7.2.1 Outer Nerve Conduits

In certain non-limiting embodiments, the nerve conduit can be configured as a sheet, wrap, tube, or another form configured for therapeutic use. The sheet, wrap, tube or other form may be a continuous surface or may comprise one or more gap or striation. As embodied herein, the device can have any suitable size, shape, and dimensions for application to the target area for implantation. For example, a sheet or tube-shaped nerve conduit can extend between peripheral nerves to cross from a proximal to a distal nerve stump. In certain embodiments, the device can be provided as a larger unit that is cut to the appropriate dimensions and shape prior to application. For example, a sheet or tube can be provided having a thickness ranging from about 50 μm to about 2 cm, or from about 1 mm to about 1 cm. When implanted in a subject, the device can be placed in a cylindrical arrangement (e.g., as a wrap or tube around a nerve). For example, such a cylindrical arrangement can have a diameter of from about 50 μm to about 2 cm or between about 1 mm and 1 cm. In particular embodiments, the nerve conduit can comprise a tube having a lumen.

Figure 3:
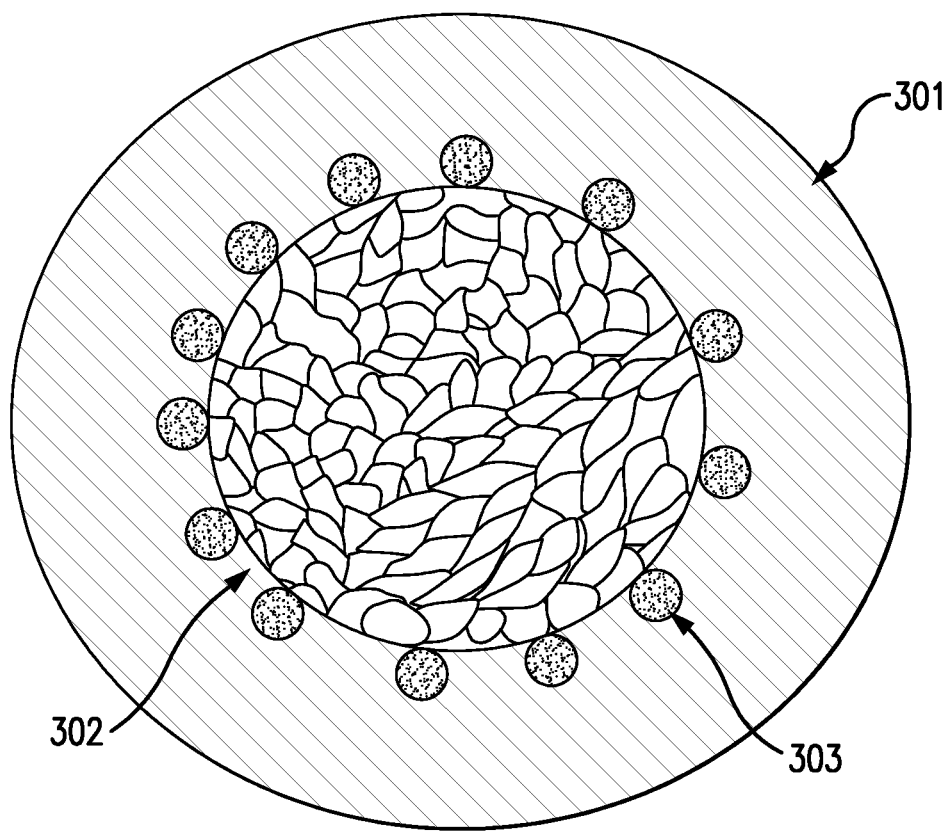
FIG. 3 is a schematic cross-section view of the nerve guide.

In certain non-limiting embodiments, the nerve conduit can include a polymer tube having a lumen. As shown in FIG. 3, the nerve conduit can comprise an inner layer 302 and an outer layer 301 having a polymer. As embodied herein, the polymer can be a biodegradable polymer. A biodegradable polymer can break down under the conditions of implantation, i.e., in the nervous system tissue environment. The biodegradable polymer and its degradation products can be biocompatible and non-toxic.

For example, and not limitation, suitable biodegradable polymers include poly(ester urethane) urea (PEUU), polycarbonate urethane urea (PCUU), poly (ether ester urethane) urea, and other degradable polyurethanes, as well as polylactic acid, poly(lactic-co-glycolic) acid, poly(caprolactone), poly(lactide), acrylic resins, polyglycolide, polylactide, polyhydroxybutyrate, poly(2-hydroxyethyl-methacrylate), poly(ethylene glycol), polydioxanone, chitosan, hyaluronic acid, hydrogels, and combinations thereof. In other non-limiting embodiments, the device can be based on a non-degradable polymer. For example and not limitation, such non-degradable polymers include silicone rubber, polyethylene, polypropylene, poly(methyl methacrylate) (PMMA), poly(tetrafluoroethylene) (PTFE), polystyrene, polyethylcyanoacrylate, poly(vinyl chloride) (PVC), polyether ether ketone (PEEK), polyether sulfone (PES), and combinations thereof. In certain embodiments, the polymeric matrix can comprise a single type of polymer or a combination of different polymers, e.g., as a polymer blend and/or copolymer. In certain embodiments, the polymeric matrix can comprise a combination of one or more biodegradable polymer and one or more non-degradable polymer. In certain embodiments, the combination of a biodegradable polymer and a non-degradable polymer can itself be biodegradable. In particular embodiments, the polymeric matrix can contain polylactic acid, poly(lactic-co-glycolic) acid and/or poly(caprolactone).

In certain non-limiting embodiments, as shown in FIG. 3, the inner layer 302 can include microspheres 303 that contain active agents. The microsphere 303 can be double-walled microsphere. The double-walled microsphere 303 can include an inner wall and an outer wall comprising a biodegradable polymer For example, and not limitation, suitable biodegradable polymers include poly(ester urethane) urea (PEUU), polycarbonate urethane urea (PCUU), poly (ether ester urethane) urea, and other degradable polyurethanes, as well as polylactic acid, poly(lactic-co-glycolic) acid, poly(caprolactone), poly(lactide), acrylic resins, polyglycolide, polylactide, polyhydroxybutyrate, poly(2-hydroxyethyl-methacrylate), poly(ethylene glycol), polydioxanone, chitosan, hyaluronic acid, hydrogels, and combinations thereof.

The order of the walls (that is to say, which polymer becomes the inner wall and which polymer becomes the outer wall) can be determined based on the principles of phase separation. For example, once solutions containing the two polymer "walls" can be mixed to form an emulsion, the polymer layer that is first to precipitate out the solvent associated therewith (i.e. the solvent that is first to evaporate) can form the core layer, and the later-precipitating polymer can form the shell. Persons of ordinary skill in the art can obtain the desired wall order based on, for example, the hydrophilicity of the solvent selected, the polarity of the solvent selected, and the solubility profile of the polymer itself. Phase separation techniques are known to those of ordinary skill in the art, and details can be found, for example, in "In vitro and in vivo degradation of double-walled polymer microspheres," Journal of Controlled Release 40:169-178 (1996), and "In vitro degradation of polyanhydride/polyester core-shell double-walled microspheres," International Journal of Pharmaceutics, 301:294-303 (2005), each of which is hereby incorporated by reference in their entirety. Double-walled microspheres 303 can be reproducibly integrated within polymer nerve conduit in manufacturer-controlled distribution. To confirm the distribution of microspheres within the nerve guide, fluorescently labeled bovine serum albumin (BSA) can be encapsulated and visualized through fluorescent microscopy.

In one embodiment, a double-walled microsphere delivery system is provided for delivery of an active agent (e.g., bioactive GDNF) with a sustained release profile of at least 1, 10, 20, 30, 40, 50, 60, 70, 80, 90, 100, 150, 200, 250, 300, 350, 400, 450, 500, 550, 600, 650, 700, 750, 800, 850, 900, 950, 1000 days or more. In particular embodiments, the double-walled microsphere 303 can release the active agent at least 80 days. In non-limiting embodiments, the double-walled microsphere can minimize an initial burst release and induce a controlled release of an active agent.

In particular embodiments, double-walled microspheres including poly(lactide) and poly(lactic-co-glycolic acid) walls can be incorporated into porous poly(caprolactone) nerve conduits. The poly(lactide) wall can be the inner wall and the poly(lactic-co-glycolic acid) wall can be outer wall. Alternatively, the poly(lactide) wall can be the outer wall and the poly(lactic-co-glycolic acid) wall can be inner wall. In certain embodiments, the double-walled microspheres 303 can include GDNF as an active agent.

Figure 4:
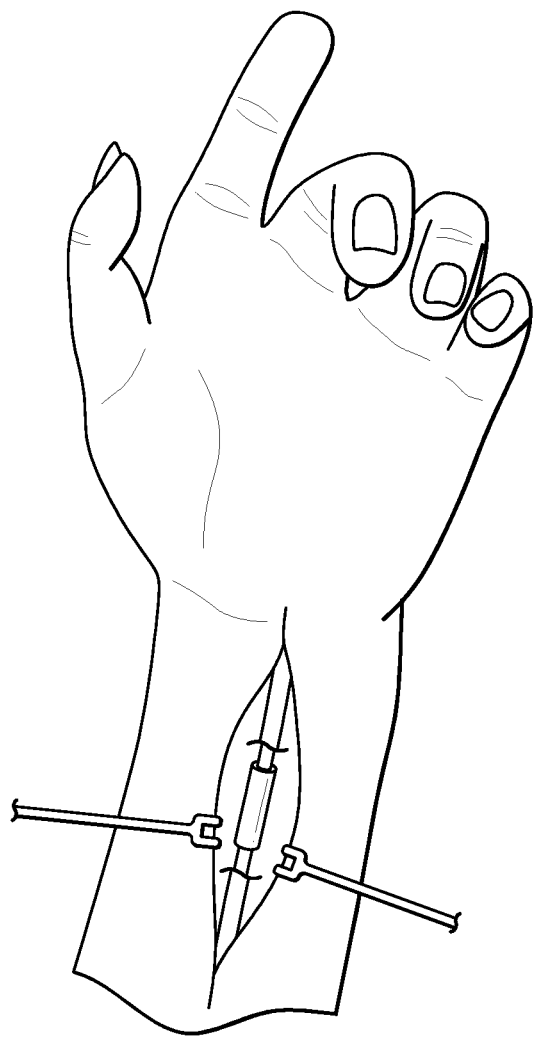
FIG. 4 is a schematic illustration of the nerve guide implanted into a median nerve defect.

The device can be suitable for implantation into a subject. The nerve conduit can be configured to be applied to an area of nervous tissue for treatment. For example, the device can be applied to a target area in the subject by covering or wrapping the target area with the device by suturing, stapling, adhering with adhesive, tying, or otherwise attaching the device to itself and/or to tissue in the target area. For example, as shown in FIG. 4, the device can be configured as a sheet that is wrapped around a target nerve and sutured in place.

Exemplary nerve conduits are disclosed in U.S. Pat. Nos. 9,750,851 and 9,498,221 which are hereby incorporated by reference in their entireties.

7.2.2 Inner Nerve Grafts

In certain aspects, the present invention can further include a nerve graft that can provide 3-dimensional extracellular matrix (ECM) structures to support cell migration during nerve regeneration (e.g., Schwann cells).

In non-limiting embodiments, the nerve graft can include an autograft (a nerve taken from another part of a patient's body), an allograft (a nerve taken from a donor of the same species as the recipient but genetically identical), an isograft (a nerve taken from an identical twin), or a xenograft (a nerve taken from another species). The nerve graft can be isolated from various subjects. Non-limiting examples of subjects include humans, mammals, pigs, horses, rats, mice, rodents, rabbits, dogs, cats, monkeys, goat, sheep, cows, deer, and other non-mammalian animals. Standard methods for isolation of a target organ are well known to the skilled artisan and can be used to isolate the organ. In particular embodiments, the nerve graft can be a human nerve allograft for bridging severed nerves without the comorbidities associated with an additional surgical site.

In certain embodiments, the nerve graft can be acellular. The nerve graft can be decellularized and processed, resulting in a surgical implant having the natural structural pathways to guide axon regeneration. Processing and decellularization of the nerve allograft can clear much of the axonal and myelin debris so that nerves may have an unimpeded pathway in which to regrow. Decellularization may be accomplished, for example, by mechanical and/or chemical and/or enzymatic means. In certain embodiments, sonication and/or freeze/thaw cycling may be used to facilitate decellularization. Chemical decellularization may be performed, for example, by a method comprising exposing a nerve graft to an effective amount of detergent. Processing also can remove material and molecules that may potentially elicit a deleterious immune response in the recipient or that could result in infection. For example, and not imitation, the obtained nerve graft can be soaked in a solution comprising one or more sulfobetaines for at least six hours and be treated with a mixture of one or more sulfobetaines and Triton X-200. Then, the nerve graft can be washed with one or more solutions of a buffered salt to remove excess detergent to form the native, acellular nerve tissue replacement. The basal laminae and endoneurium layer substantially retain the native extracellular matrix structure.

In non-limiting embodiments, the nerve graft can undergo a combination of treatments including gamma irradiation (or another means of removing potential pathogens or other microbes) as well as mechanical and chemical decellularization (e.g. detergent-processing). In some embodiments, the processed nerve graft can further undergo enzymatic digestion of chondroitin sulfate proteoglycan (CSPG), a known inhibitor of axonal growth, through acute treatment with chondroitinase ABC. Prior studies have demonstrated that treating donor nerve tissue with chondroitinase effectively reduced the quantity of CSPG, and increased axonal regeneration through resulting acellular grafts in vivo. For example, an acellular nerve graft may be obtained by removing nerve segments from the cadaver of an animal of the same species (here, typically human), and processing or treating them using various techniques to remove cellular and noncellular factors such as cells, fat, blood, axonal debris and chondroitin sulfate proteoglycans while preserving the three-dimensional scaffold and basal lamina tubular structure of the nerve.

Nerve grafts can have a variety of lengths and diameters depending on source and intended use. For example, a nerve graft can have a diameter up to about 0.1 mm, about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, and about 10 mm. In particular embodiments, the nerve graft can have a diameter up to about 5 mm. Further, a nerve graft can have a diameter of at least about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, and about 10 mm. In certain embodiments, a nerve graft can have a diameter between about 0.5 mm and about 10 mm, or between about 0.5 mm and about 5 mm, or between about 1 mm and about 5 mm. Furthermore, the nerve graft can have a length of at least about 5 mm, about 10 mm, or about 50 mm, and up to about 50 mm, about 100 mm, about 500 mm, about 1 cm, about 3 cm, about 5 cm, or about 10 cm or longer. In particular embodiments, the length of the nerve graft can be up to about 5 cm. In certain embodiments, the nerve graft may have a length between about 1 cm and about 8 cm, or between about 2 cm and about 8 cm, or between about 3 cm and about 8 cm.

7.2.3 Active Agents

The presently disclosed invention can deliver an active agent which enhances regeneration and overcomes current limitations in nerve repair across large defects. For example, and not limitation, the nerve conduit can include Glial Cell Line-Derived Neurotrophic Factor (GDNF) which is a promoter of axonal elongation and branching. GDNF has been shown to promote Schwann cell proliferation and migration. Other nerve factors that can be comprised in the microspheres 303 include, but are not limited to, glial growth factor 2 (GGF2), brain-derived neurotrophic factor (BDNF), novel neurotrophin-1 (NNT1), Ciliary neurotrophic factor (CNTF), nerve growth factor (NGF), and neurotrophin-3 (NT-3). These agents, or a combination thereof, can be provided in addition to, or in place of, GDNF. In non-limiting embodiments, the active agents can repopulate nerve cells (e.g., Schwann cells) and promote innervation of defected muscles. Non-limiting exemplary active agents are disclosed in U.S. Pat. Nos. 9,750,851 and 9,498,221, which are hereby incorporated by reference in their entirety.

7.3 Methods of Making Such Devices

The presently disclosed subject matter also provides methods of making a composite nerve guide. In one embodiment, the method includes forming a first mixture (e.g., a solution) of a first polymer and a first solvent, and separately, forming a mixture (e.g., a solution) of a second polymer and a second solvent. The first or second polymer, which can form a wall of the double walled microsphere can be, for example, poly(1-lactide), poly(lactic-co-glycolic acid), poly (1,3-bis-(p-carboxyphenoxy propane)-co-(sebacic anhydride) (e.g., 20:80 PCPP:SA), poly(fumaric-co-sebacic) anhydride, and poly[(1,6-bis-carboxyphenoxy) hexane]. The first or second solvent can be, for example, water dichloromethane, ethyl acetate, diethyl ether, THF, acetone and EMSO. For example, in an alternative embodiment, poly (lactic acid) can form the external layer and poly(1,3-bis-(p-carboxyphenoxy propane)-co-(sebacic anhydride) (e.g., 20:80 PCPP:SA) can form the core layer.

After a polymer is added to the mixture, and preferably after the polymer is fully dissolved, an active agent (e.g., GDNF) can be added to the first and/or second mixture. Alternatively, a component that is readily discernable (e.g., fluorescently-labeled bovine serum albumin) can be added in place of, or in addition to, the active agent for purposes of testing. Examples of active agents that can be added to the first and/or second mixture, and ultimately the nerve conduit itself can include neurotrophic factors, such as, but not limited to, glial cell-line derived neurotrophic factor (GDNF), brain-derived neurotrophic factor (BDNF), novel neurotrophin-1 (NNT1), Ciliary neurotrophic factor (CNTF), and neurotrophin-3 (NT-3). After adding the active agent, the mixture can be vortexed for a period of time (e.g., less than a minute) to achieve a homogenous mixture. An emulsifier such as docusate sodium salt can also be added to the first and/or second mixtures. An emulsifier, such as docusate sodium, or other stabilizer can be added to the first and/or second mixtures to stabilize the protein.

The two mixtures can then be combined, and optionally vortexed. When poly(lactide) and poly(lactic-co-glycolic acid) polymers are used as wall-forming polymers and dichloromethane is used as the solvent for the first two mixtures, an oil-in-oil emulsion is formed upon combining the two mixtures. The combined mixtures can be gradually added to a third solvent (e.g., drop-wise using a Pasteur pipette) to form a third mixture and then vigorously stirred for a few hours (e.g., stirred at 900 rpm for 3 hours). An aqueous solvent such as an aqueous solution of 0.5% poly (vinyl alcohol) can be used as the third solvent.

When polymer mixtures are combined to form the third mixture (e.g., an emulsion), the polymer that is associated with the solvent that is the first to evaporate can form the core of the microsphere, and the polymer that is associated with the solvent that is the last to evaporate can form the shell of the microsphere and at least substantially encapsulate the core polymer wall. In embodiments in which poly (lactide) and poly(lactic-co-glycolic acid) polymers are used as wall-forming polymers and dichloromethane can be used as the solvent for the first two mixtures, the poly(lactic-co-glycolic acid) polymer will form the core layer, and the poly(lactide) will form the shell layer.

In certain embodiments, microspheres can be formed in the third mixture, which can be isolated, for example, by centrifugation and washing. For example, the third mixture can be centrifuged for about 10 minutes and washed with water, and then repeated. The microspheres obtained from the isolation step can then be lyophilized and stored at a low temperature in a desiccant.

Nerve conduit to which the double-walled microspheres can be added, such as nerve guides can be prepared according to known methods. For example, double walled microspheres and nerve guides can be prepared as generally disclosed in Kokai et al., Diffusion of soluble factors through degradable polymer nerve guides: controlling manufacturing parameters, Acta Biomater 2009; 5(7):2540-50, which is hereby incorporated by reference.

In certain embodiments, polycaprolactone nerve guides can be prepared by coating glass capillary mandrels with an aqueous polymer solution (e.g., a 17% w/v aqueous solution of poly(vinyl alcohol)). The coated capillary mandrels can then be introduced to a polymer slurry of polycaprolactone dissolved in an organic solvent (e.g., ethyl acetate) to which sodium chloride or other leaching salt has been added. The organic solvent can be allowed to evaporate, and the mandrel can be dipped in the polymer slurry. The resulting polymer conduits can be immersed in distilled water, and the polymer subsequently removed from the glass mandrels. The thickness of the polymer nerve guide can be varied based on the number of immersions in the polymer slurry. For example, six immersions in polymer slurry yielded a nerve guide wall thickness of about 600 µm-about 700 µm.

The double-walled microspheres can be added to the medical device by introducing the microspheres to the medical device in between immersions in the polymer slurries. For example, the semi-dried, dip-coated medical device can be introduced to microspheres that are even spread across a non-reactive surface by rolling, or by similar means, and allowed to dry before subsequent dip-coating. Any technique can be used to apply the microspheres to the biodegradable, yet otherwise inert polymer (e.g. polycaprolactone) so long as the process does not dissolve or otherwise negatively impact the microspheres. For example, processes requiring high temperatures should be disfavored, unless the microspheres can be protected. Electrospinning and polymer casting techniques known to those of ordinary skill in the art can be used.

In non-limiting embodiments, nerve grafts can be isolated from various subjects. The isolated grafts can be decellularized and processed, resulting in a surgical implant having the natural structural pathways to guide axon regeneration. In particular embodiments, the polymer nerve conduit with double-walled microspheres containing neurotrophic factors can wrap around decellularized nerve graft, or, where the nerve conduit is configured as a tube, the nerve graft can be introduced into the lumen of the tube or the nerve conduit may be formed around the nerve graft.

Exemplary methods of making nerve conduits are disclosed in U.S. Pat. Nos. 9,750,851 and 9,498,221, which are hereby incorporated by reference in their entirety.

The invention further provides for kits that comprise materials for producing the composite nerve guides disclosed herein. In certain embodiments, a kit may comprise a composite nerve guide and suture material. In certain embodiments, a kit may comprise, separately, an outer conduit and an inner nerve graft, which may be cut to size and combined prior to use.

7.4 Methods of Treatment

The present invention also relates to methods of treating injuries to nervous system tissue comprising introducing a composite nerve guide as described above into an area of injury or disease. Injury may be caused, for example, by accidental or surgical trauma, infarction, infection, and/or inflammation.

The methods can include treating any type of nervous system tissue where growth of neuronal processes, e.g. axons, may be desirable. In certain non-limiting embodiments, the target nervous system tissue is a nerve which may be a nerve of the CNS such as a cranial nerve or spinal nerve or may be a peripheral nerve of the PNS. Non-limiting examples of nerves include the abdominal aortic plexus, abducens nerve, accessory nerve, accessory obturator nerve, Alderman's nerve, anococcygeal nerve, ansa cervicalis, anterior interosseous nerve, anterior superior alveolar nerve, Auerbach's plexus, auriculotemporal nerve, axillary nerve, brachial plexus, buccal nerve, cardiac plexus, cavernous plexus, celiac ganglion, cervical plexus, chorda tympani, ciliary ganglion, coccygeal nerve, cochlear nerve, common fibular nerve, common palmar digital nerve, cutaneous nerve, deep fibular nerve, deep petrosal nerve, deep temporal nerves, dorsal scapular nerve, esophageal plexus, ethmoidal nerve, external laryngeal nerve, external nasal nerve, facial nerve, femoral nerve, frontal nerve, gastric plexuses, geniculate ganglion, genitofemoral nerve, glossopharyngeal nerve, greater auricular nerve, greater occipital nerve, greater petrosal nerve, hepatic plexus, hypoglossal nerve, iliohypogastric nerve, ilioinguinal nerve, inferior alveolar nerve, inferior anal nerve, inferior cardiac nerve, inferior cervical ganglion, inferior gluteal nerve, inferior hypogastric plexus, inferior mesenteric plexus, inferior palpebral nerve, infraorbital nerve, infraorbital plexus, infratrochlear nerve, intercostal nerves, intercostobrachial nerve, intermediate cutaneous nerve, internal carotid plexus, internal laryngeal nerve, interneuron, jugular ganglion, lacrimal nerve, lateral cord, lateral pectoral nerve, lateral plantar nerve, lateral pterygoid nerve, lesser occipital nerve, lingual nerve, long ciliary nerve, long thoracic nerve, lower subscapular nerve, lumbar nerve, lumbar plexus, lumbar splanchnic nerve, lumboinguinal nerve, lumbosacral plexus, lumbosacral trunk, mandibular nerve, masseteric nerve, maxillary nerve, medial cord, medial cutaneous nerve, medial pectoral nerve, medial plantar nerve, medial pterygoid nerve, median nerve, Meissner's plexus, mental nerve, middle meningeal nerve, motor nerve, musculocutaneous nerve, mylohyoid nerve, nasociliary nerve, nasopalatine nerve, nerve of pterygoid canal, nerve to obturator internus, nerve to quadratus femoris, nerve to the piriformis, nerve to the stapedius, nerve to the subclavius, nervus intermedius, nervus spinosus, nodose ganglion, obturator nerve, occipital nerve, oculomotor nerve, olfactory nerve, ophthalmic nerve, optic nerve, otic ganglion, ovarian plexus, palatine nerve, pancreatic plexus, patellar plexus, pelvic splanchnic nerves, perforating cutaneous nerve, perineal nerve, petrous ganglion, pharyngeal nerve, pharyngeal plexus, phrenic nerve, phrenic plexus, posterior auricular nerve, posterior cord, posterior scrotal nerve, posterior superior alveolar nerve, prostatic plexus (nervous), pterygopalatine ganglion, pudendal nerve, pudendal plexus, radial nerve, recurrent laryngeal nerve, renal plexus, sacral plexus, sacral splanchnic nerves, saphenous nerve, sciatic nerve, semilunar ganglion, sensory nerve, short ciliary nerve, sphenopalatine nerve, splenic plexus, subcostal nerve, submandibular ganglion, suboccipital nerve, superficial fibular nerve, superior cardiac nerve, superior cervical ganglion, superior gluteal nerve, superior hypogastric plexus, superior labial nerve, superior laryngeal nerve, superior mesenteric plexus, superior rectal plexus, supraclavicular nerve, supraorbital nerve, suprarenal plexus, suprascapular nerve, supratrochlear nerve, sural nerve, sympathetic trunk, thoracic aortic plexus, thoracic splanchnic nerve, thoraco-abdominal nerve, thoracodorsal nerve, tibial nerve, transverse cervical nerve, trigeminal nerve, trochlear nerve, tympanic nerve, ulnar nerve, upper subscapular nerve, uterovaginal plexus, vagus nerve, ventral ramus, vesical nervous plexus, vestibular nerve, vestibulocochlear nerve, zygomatic nerve, zygomaticofacial nerve, and zygomaticotemporal nerve. In particular embodiments, the nervous system tissue is the sciatic nerve. In particular embodiments, the nervous system tissue is a bundle of axons in the spinal cord.

In certain embodiments, the invention provides for a method of treating an injury to a nerve, wherein a proximal and a distal end of the nerve are separated by a gap, comprising introducing, into the gap, a composite nerve guide as described herein. In certain non-limiting embodiments, the composite nerve guide, when placed, covers at least about 50 percent, or at least about 75 percent, or at least about 80 percent, or at least about 90 percent, of the gap between the proximal and distal nerve ends. In certain non-limiting embodiments, the gap is at least about 1 cm. In certain non-limiting embodiments, the gap is at least about 2 cm. In certain non-limiting embodiments, the gap is at least about 3 cm. In certain non-limiting embodiments, the gap is at least about 4 cm. In certain non-limiting embodiments, the gap is at least about 5 cm. In certain non-limiting embodiments, the gap is up to about 3 cm. In certain non-limiting embodiments, the gap is up to about 4 cm. In certain non-limiting embodiments, the gap is up to about 5 cm. In certain non-limiting embodiments, the gap is up to about 6 cm. In certain non-limiting embodiments, the gap is up to about 8 cm. In certain non-limiting embodiments, the gap is up to about 10 cm.

In certain embodiments, the invention provides for a method of promoting regeneration of a nerve, wherein a proximal and a distal end of the nerve are separated by a gap, comprising introducing, into the gap, a composite nerve guide as described herein. In certain non-limiting embodiments, the composite nerve guide, when placed, covers at least about 50 percent, or at least about 75 percent, or at least about 80 percent, or at least about 90 percent, of the gap between the proximal and distal nerve ends. In certain non-limiting embodiments, the gap is at least about 1 cm. In certain non-limiting embodiments, the gap is at least about 2 cm. In certain non-limiting embodiments, the gap is at least about 3 cm. In certain non-limiting embodiments, the gap is at least about 4 cm. In certain non-limiting embodiments, the gap is at least about 5 cm. In certain non-limiting embodiments, the gap is up to about 3 cm. In certain non-limiting embodiments, the gap is up to about 4 cm. In certain non-limiting embodiments, the gap is up to about 5 cm. In certain non-limiting embodiments, the gap is up to about 6 cm. In certain non-limiting embodiments, the gap is up to about 8 cm. In certain non-limiting embodiments, the gap is up to about 10 cm.

In certain embodiments, the invention provides for a method of promoting axonal regrowth, wherein a proximal and a distal end of a group of axons are separated by a gap, comprising introducing, into the gap, a composite nerve guide as described herein. In certain non-limiting embodiments, the composite nerve guide, when placed, covers at least about 50 percent, or at least about 75 percent, or at least about 80 percent, or at least about 90 percent, of the gap between the proximal and distal nerve ends. In certain non-limiting embodiments, the gap is at least about 1 cm. In certain non-limiting embodiments, the gap is at least about 2 cm. In certain non-limiting embodiments, the gap is at least about 3 cm. In certain non-limiting embodiments, the gap is at least about 4 cm. In certain non-limiting embodiments, the gap is at least about 5 cm. In certain non-limiting embodiments, the gap is up to about 3 cm. In certain non-limiting embodiments, the gap is up to about 4 cm. In certain non-limiting embodiments, the gap is up to about 5 cm. In certain non-limiting embodiments, the gap is up to about 6 cm. In certain non-limiting embodiments, the gap is up to about 8 cm. In certain non-limiting embodiments, the gap is up to about 10 cm.

8. EXAMPLES

The following Examples are offered to more fully illustrate the disclosure but are not to be construed as limiting the scope thereof.

Example 1

In Vivo Effects of Device on Regeneration of Sciatic Nerve Located in Hind Limb of Rats This Example illustrates the use of a composite nerve guide for regeneration of sciatic nerve located in hind limb of rats.

Materials and Methods

Reagents and materials: All chemicals were analytical grade or purer and were purchased from commercial suppliers. Poly(vinyl alcohol) (average Mw 9000-10,000, 80% hydrolyzed), poly(DL-lactide-co-glycolide) (lactide:glycolide (50:50), mol wt 40,000-75,000 units), poly(caprolactone) (Mw 65,000), Fluorescein isothiocyanate conjugated Bovine Albumin (A9771) (FITC-BSA), lysozyme from chicken egg white, Dichloromethane, Ethyl Acetate, Gel Mount (G0918), Xylene, monoclonal anti-S100, and Phosphate Buffered Saline (PBS) were all purchased from Sigma-Aldrich (St. Louis, Mo.). Poly-L-lactide (0.90-1.20 dL/g) was purchased from DURECT Corporation (Pelham, Ala.). The Micro Bicinchoninic Acid (BCA) Protein Assay Kit (23235) was purchased from Pierce (Rockford, Ill.). The Masson's trichrome kit was purchased from American MasterTech (Modesto, Calif.). The GDNF Emax Immuno-Assay Systems Kit was purchased from Promega (Madison, Wis.). Recombinant human Glial-Derived Neurotrophic factor (GDNF) produced in *E. coli* was purchased from Leinco Technologies (St. Louis, Mo.) and MedGenesis. Human nerve allografts were purchased from commercial supplier (AxoGen).

Fabrication of poly(caprolactone) disks and nerve conduits: Poly(caprolactone) (PCL) disks were prepared to determine the effect of nerve guide macrostructure on lysozyme release from the microspheres. Briefly, 15 mg of microspheres were added to a circular well (diameter ¼ 1 cm, depth ¼ 0.5 cm) of a custom-made silicone mold. Porous disks were created by dissolving 1.35 g PCL in 15 mL ethyl acetate. To the dissolved polymer solution, sodium chloride impregnation was accomplished by adding NaCl in a 80% (v/v) amount 200 ml of the polymer slurry was added to each mold and mixed well to distribute the microspheres within the disk space. The ethyl acetate was allowed to evaporate, and the sodium chloride was leached with distilled water.

Fabrication of and nerve conduits: PCL nerve guides were fabricated using a modification of previously reported methods [18]. Glass capillary mandrels 1.5 mm in diameter were coated with a 17% w/v % aqueous solution of poly(vinyl alcohol) (PVA), air dried and then immersed into the polymer slurry (as described above) creating NaCl/PCL mandrel coatings. The ethyl acetate was allowed to evaporate for a minimum of 10 min between successive mandrel immersions into the polymer slurry. After the completion of the dip-coating process, the resulting polymer conduits were submerged in distilled water to allow for salt and PVA dissolution, and the guides were removed from the glass mandrels. The final wall thickness after 6 successive immersions of the mandrels into the polymer solutions was 600-700 mms. To incorporate double-walled microspheres into the inner half of the nerve guide conduit, 15 mg of microspheres were evenly spread onto a drawn grid on parchment paper. After the first immersion of the glass mandrel into the PCL slurry, the ethyl acetate was allowed to evaporate for only 30 s leaving a semihardened polymer layer on the mandrel. This was then smoothly rolled across the microspheres on parchment paper. The PCL with embedded microspheres was allowed to dry for 10 min and then repeatedly coated with additional layers of polymer as done in nerve guides without microspheres.

Fabrication of double-walled microspheres. To create double-walled microspheres, a 17.5% poly(lactic-co-glycolic acid) (PLGA) solution was created with 150 mg PLGA in dichloromethane. In a separate glass scintillation vial, a 10% solution of poly(lactide) (PLLA) of equal polymer mass was prepared. After both polymers were fully dissolved, either 4 mg of FITC-BSA or 20 mG of lysozyme was added to the PLGA solution and vortexed for ~30 s to achieve a homogenous mixture. The PLGA solution was then combined with the PLA solution and vortexed for an additional 60 s. This oil-in-oil emulsion was added dropwise through a Pasteur pipette to 200 mL of aqueous 0.5% poly(vinyl alcohol) solution stirring at 900 rpm for 3 h. Then, the polymer microspheres were collected through centrifugation (1500 g for 10 min) and washed three times. Finally, the microspheres were lyophilized using a Labconco freeze dry system (without a cryoprotectant) and stored in a desiccant at ~20° C. To encapsulate glial cell line-derived neurotrophic factor (GDNF), a solution of 40 ml (0.1 mg/mL) of GDNF, 100 mg of docusate sodium salt and 7 mg human serum albumin was prepared in 0.5 mL sterile water over ice (formulation adapted from [19]). After mixing well, the solution was frozen and lyophilized. The protein/surfactant mixture was then added to PLGA already dissolved in dichloromethane and microspheres were prepared as described for lysozyme encapsulation.

GDNF release from double-walled microspheres: To determine the release kinetics of GDNF from the PLGA/PLA double-walled microspheres, 10 mg of microspheres were placed into Eppendorf tubes and incubated in 1 mL PBS at 37° C. At specified time points, the microspheres were vortexed, centrifuged for 10 min at 1500 g and the supernatant was replaced with fresh PBS. The amount of soluble GDNF in the collected samples was analyzed using an enzyme linked immunosorbent assay (ELISA) manufacturer's instructions. The optical density was recorded at 450 nm in an ELISA plate reader (Tecan, N.C.). The GDNF concentrations were calculated against a 6-point standard curve, then adjusted to picograms of GDNF per milligram of microspheres.

Surgical methods: Following the guidelines of the University of Pittsburgh Institutional of Animal Care and Use Committee, 8 male Lewis rats (250-300 g, Harlan Labs) were used to evaluate the initial efficacy of the composite nerve guide for improved nerve regeneration. To implant the guide, each rat was anesthetized with an intraperitoneal injection of sodium pentobarbital (50 mg/kg). The sciatic nerve was then exposed with a muscle splitting incision of the gluteal muscle. The nerve was sharply transected ~1.5 cm from the proximal bifurcation and 1.5 cm of tissue was excised. After the proximal and distal nerve stumps were allowed to retract, the exposed fascicles were trimmed and sutured with 10-0 prolene epineurial mattress stitch 1 mm into each end of a 1.7 cm nerve guide, creating a 1.5 cm defect (FIGS. 5A and 5B) The gluteal muscle and skin were then closed with 4-0 vicryl suture. The animals were randomly divided evenly amongst four groups: a reverse polarity autograft (positive control), a decellularized nerve allograft, a composite guide with containing empty microspheres (no drug), and the composite guide with GDNF microspheres.

Rats were implanted with one of the treatments in Table 1 on the sciatic nerve. Table 1 provides the sample size of each treatment group.

TABLE 1

| Treatment | Number (n) |
| --- | --- |
| Composite Guide with Double-Walled Microspheres | 8 |
| Decellularized Nerve Allograft | 8 |
| Autograft | 8 |
| Empty Composite Guide | 8 |

Electrophysiology Analysis:

Animals were anesthetized with sodium pentobarbitol and the injured sciatic nerve was exposed with a muscle splitting incision made following the scar line remaining from graft or guide implantation. After freeing the isograft or regenerated nerve from the superficial and underlying muscle tissues, a bipolar nerve cuff electrode was placed around the nerve. Because the implanted nerve conduit enclosed the regenerated nerve, the PCL material had to be carefully removed such that sufficient nerve material was available for contact with the nerve cuff. The lower gastrocnemius was then isolated from the anterior and posterior tibialis muscles and the Achilles tendon was cut and fastened to a force transducer using a transfixation stitch and silk sutures (FIGS. 6A and 6B). To completely stabilize the femur position, the animal's foot, knee, and back were immobilized on the data acquisition board using gauge needles.

Histological analysis: After 6 weeks, the animals were sacrificed with an overdose of sodium pentobarbital and the implanted guides were harvested and immediately fixed in 4% paraformaldehyde. After the tissue was fixed for at least 24 h, the nerve samples were washed with PBS and fixed in 1% osmium tetroxide for at least 2 h. After the nerve specimens were dehydrated with increasing concentrations of ethanol (30-100%), the nerves were sectioned with a sharp razor blade at the proximal nerve stump (PS), the proximal (PG), middle (MG) and distal (DG) regions of the nerve conduit, and at the distal nerve stump (DS). The sections were then embedded in paraffin in descending order and sectioned at 3 mm in thickness.

Masson's trichrome: For analysis of cellular and tissue infiltration of the nerve conduits, nerve sections from the negative control and experimental animals were stained for Masson's Trichrome. Sectioned nerves were first deparaffinized with xylene and rehydrated with decreasing percent alcohol solutions (100% followed by 90% and then DI water). Solutions from a Masson's trichrome kit were then used according to the protocol published by Di Scipio et al. [20].

Immunohistochemistry: For fluorescent visualization of Schwann cells, immunohistochemistry was performed on explanted nerve samples. Paraffin embedded specimens fixed in osmium tetroxide were first deparaffinized as described above and then etched with $H_2O_2$ for 10 min as described in [24]. The samples were then blocked with 5% FBS with 0.02% triton-X in PBS for 1 h at room temperature. Antibodies against S-100 protein were then added overnight at 4° C. (1:400 in 2.5% FBS and 0.02% triton-X in PBS). The samples were then washed three times with PBS and the secondary antibody was added for 1 h at room temperature (1:1000 in 2.5% FBS and 0.02% triton-X in PBS). The samples were then washed thrice again and the nuclei were detected using DAPI (0.6 mg/mL). The slides were then mounted with a fluorescent mounting media.

Statistical analysis: A minimum repetition value of five was used when measuring lysozyme release from PCL disks and nerve guides. Results are expressed as the mean±standard deviation. Analysis of variance (ANOVA) was used to determine statistical significance between experimental groups. The least significant difference method was used for multiple comparisons with $p<0.05$.

Results And Discussion

A 1.5 cm defect was created on the sciatic nerve located in the hind limb of rats. The defect was repaired with one of four treatment groups: a reverse polarity autograft (positive control), a decellularized nerve allograft, a composite guide with containing empty microspheres (no drug), and the composite guide with GDNF microspheres. FIG. 5C shows an exemplary composite guide implanted into sciatic nerve. As shown in FIG. 5D, the implanted composite nerve guide was able to maintain structural integrity at 6 weeks postoperatively To assess the efficacy of the composite, guide the gastrocnemius muscle weight ratio (GWR) between treatment groups at 6 weeks postoperatively were evaluated. GWR is the weight of the operated gastrocnemius muscle normalized to naïve gastrocnemius muscle weight. The gastrocnemius muscle is innervated by the sciatic nerve and thus atrophies when the nerve is compromised. At 6-weeks postoperatively, a significant increase in Gastrocnemius Muscle Weight Ratio was observed with GDNF Composite Guide compared to decellularized nerve allograft and empty composite guide suggesting that the delivered GDNF has a protective effect on gastrocnemius muscle atrophy (FIGS. 7A and 7B). A trend towards increased muscle weight was observed with GDNF composite guide treatment compared to autograft positive control ($p=0.051$). Importantly, no decrease in GWR was observed with wrapping a nerve conduit guide around decellularized nerve allograft. This indicates that the presence of the nerve conduit around the decellularized graft does not appear to impact regeneration through the graft. Furthermore, a significant increase in gastrocnemius muscle weight compared to the control treatment suggests the composite nerve guides with double-walled microspheres (e.g., AxoMax™) can regenerate across the gap quicker resulting in less muscle atrophy over the regeneration process as seen by the lager GWR at 6-weeks postoperatively.

Long-term release studies of GDNF from the nerve guides with double-walled microspheres were performed to approximate the release profile of the growth factor. Nerve guides embedded with double-walled microspheres encapsulating GDNF were incubated in PBS and released growth factor was quantified using an enzyme linked immunosorbent assay (ELISA) system. For example, to determine the release kinetics of GDNF from the guides, samples were placed into Eppendorf tubes and incubated in 1 mL PBS at 37° C. At certain time points, the samples were vortexed, centrifuged for 10 min at 1500 g and the supernatant was replaced with fresh PBS. The amount of soluble GDNF in the collected samples was analyzed using an ELISA manufacturer's instructions. The optical density was recorded at 450 nm in an ELISA plate reader (Tecan, N.C.). As shown in FIG. 8, the release of GDNF from the PCL nerve guides did not exhibit the typical burst release profile seen in single-walled microsphere studies. The composite guide with double-walled microspheres (e.g., AxoMax™) demonstrated a slower release of GDNF compared to PCL/GDNF. These results demonstrate that the composite guide with double-walled microspheres can support nerve regeneration over longer time periods.

Figure 9A:
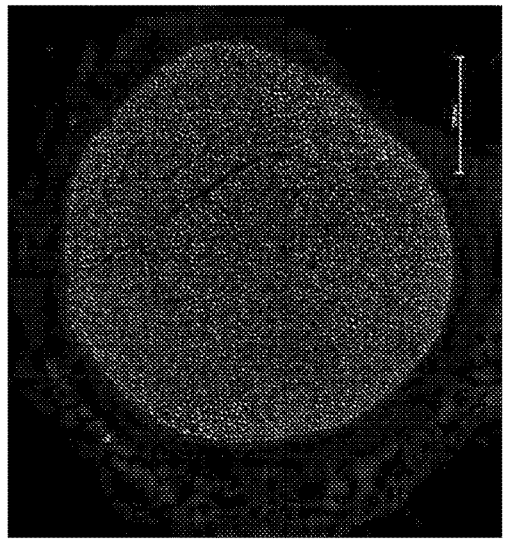
Figure 9B:

Immunohistochemistry (IHC) staining was performed to compare the amounts of neurofilament and Schwann cells within the nerve between treatment groups (FIGS. 9A-E). Neurofilament provides structural support to neurons and are important components of growth and the transmission of electrical impulses along the nerve. Schwann cells support nerve regeneration and insulate the nerve axons. When a nerve is damaged, Schwann cells will guide regeneration towards the target and therefore reconnect the two severed ends to re-innervate the target muscle. Detection of Schwann cell localization with immunofluorescence indicated that Schwann cells were present in proximal segments of the composite nerve guides. The IHC staining demonstrated increased nerve fiber density and Schwann cell density in decellularized nerves and composite guides with double-walled microspheres. Fluorescent micrographs of the composite nerve guides with GDNF microspheres show a population of Schwann cells encircling the microspheres, an indication of targeted migration of Schwann cells toward a source of GDNF (FIG. 9C). Acellular response to the encapsulated growth factor suggests that the released GDNF is bioactive and has not been completely denatured through the nerve guide fabrication process. The migration of Schwann cells, presumably from the lumen of the conduit, indicates that GDNF is being delivered to the lumen of the nerve guide in a physiologically relevant concentration and is not entirely entrapped within the porous nerve guide structure.

A Masson's Trichrome stain on the sectioned nerve samples (FIGS. 10A-D) showed nuclei and the structure of connective tissues such as collagen within the sample. Collagen is important in peripheral nerve regeneration to regulate Schwann cell function and to form the extracellular matrix. Results show that tissue integration within GDNF releasing nerve guides was improved with a greater concentration of intercellular fibers and collagen content. Furthermore, a localization of Schwann cells around microspheres encapsulating GDNF indicates that bioactive GDNF was being released from our delivery system.

Implantation of nerve guides across a 1-3 cm defect in a rat sciatic nerve gap resulted in an increase in tissue integration in both the proximal and distal segments of the lumen of the nerve guide after 6 weeks. In addition, transverse sections of the distal region of the explanted guides showed the presence of Schwann cells while none were detectable in negative control guides. Migration of Schwann cells to double-walled microspheres indicated that bioactive GDNF was encapsulated and delivered to the internal environment of the nerve guide. Because GDNF increased tissue formation within the nerve conduit lumen and also promoted the migration and proliferation of Schwann cells, the presently disclosed nerve guides can promote nerve regeneration beyond that capable with pre-existing nerve guides. Furthermore, the presently disclosed nerve guide can bridge long gap peripheral nerve defects (i.e. gaps greater than 3 cm) beyond the range of the never defects that capable with pre-existing nerve guides by using the nerve grafts. Taken together, this data demonstrates that the composite guide has the potential enhance both motor and sensory recovery after long gap peripheral nerve injuries as compared to the gold standard, autograft or allograft.

9. REFERENCES

1. Christopher T, Diane B, Bradford J, Timothy D. The Incidence of Peripheral Nerve Injury in Extremity Trauma. Am J Phys Med Rehabil: 2008; 87(5): 381-385.
3. Kim D, Midha R, Murovic J, Spinner R. Nerve injuries: operative results from major nerve injuries, entrapments, and tumors. 2nd ed. Philadelphia: Saunders Elsevier; 2008. pp. 1-611.
4. Schlosshauer B, Dreesmann L, Schaller H-E, Sinis N. Synthetic nerve guide implants in humans: a comprehensive survey. Neurosurgery 2006; 59(4): 740-8.
5. Fine E G, Decosterd I, Papaloizos M, Zurn A D, Aebischer P. GDNF and NGF released by synthetic guidance channels support sciatic nerve regeneration across a long gap. Eur J Neurosci 2002; 15(4):589-601.
6. Bloch J, Fine E G, Bouche N, Zurn A D, Aebischer P. Nerve growth factor- and neurotrophin-3-releasing guidance channels promote regeneration of the transected rat dorsal root. Exp Neurol 2001; 172(2):425-32.
7. Xu X, Yee W-C, Hwang P Y K, Yu H, Wan A C A, Gao S, et al. Peripheral nerve regeneration with sustained release of poly(phosphoester) microencapsulated nerve growth factor within nerve guide conduits. Biomaterials 2003; 24(13):2405-12.
8. Rosner B I, Siegel R A, Grosberg A, Tranquillo R T. Rational design of contact guiding, neurotrophic matrices for peripheral nerve regeneration. Ann Biomed Eng 2003; 31(11):1383-401.
9. Goraltchouk A, Scanga V, Morshead C M, Shoichet M S. Incorporation of protein-eluting microspheres into biodegradable nerve guidance channels for controlled release. J Control Release 2006; 110(2):400-7.
10. Singh M, Morris C P, Ellis R J, Detamore M S, Berkland C. Microsphere-based seamless scaffolds containing macroscopic gradients of encapsulated factors for tissue engineering. Tissue Eng Part C Methods 2008; 14(4):299-309.
11. Dodla M C, Bellamkonda R V. Differences between the effect of anisotropic and isotropic laminin and nerve growth factor presenting scaffolds on nerve regeneration across long peripheral nerve gaps. Biomaterials 2008; 29(1):33-46.
12. Chen M-H, Chen P-R, Chen M-H, Hsieh S-T, Lin F-H. Gelatin-tricalcium phosphate membranes immobilized with NGF, BDNF, or IGF-1 for peripheral nerve repair: an in vitro and in vivo study. J Biomed Mater Res A 2006; 79A(4):846-57.
13. Wood M, Borschel G, Sakiyama-Elbert S E. Controlled release of glial-derived neurotrophic factor from fibrin matrices containing an affinity-based delivery system. J Biomed Mater Res A 2009; 89A(4):909-18.
14. Lee A C, Yu V M, Lowe J B, Brenner M J, Hunter D A, Mackinnon S E, et al. Controlled release of nerve growth factor enhances sciatic nerve regeneration. Exp Neurol 2003; 184(1):295-303.
15. Newman J, Verity A, Hawatmeh S, Fee W J, Terris D. Ciliary neurotrophic factors
enhances peripheral nerve regeneration. Arch Otolaryngol Head Neck Surg 1996; 122(4):399-403.
16. Lewin S U, DS, Cheng E T, Verity A N, Terris D J. Simultaneous treatment with BDNF and CNTF after peripheral nerve transection and repair enhances rate of functional recovery compared with BDNF treatment alone. Laryngoscope 1997; 107(7):992-9.
17. Willerth S M, Sakiyama-Elbert S E. Approaches to neural tissue engineering using scaffolds for drug delivery. Adv Drug Deliv Rev 2007; 59(4-5):325-38.
18. Kokai L E, Lin Y-C, Oyster N M, Marra K G. Diffusion of soluble factors through
degradable polymer nerve guides: controlling manufacturing parameters.
Acta Biomater 2009; 5(7):2540-50.
19. Jiang C, Moore M, Zhang X, Klassen H, Langer R, Young M. Intravitreal injections
of GDNF-loaded biodegradable microspheres are neuroprotective in a rat model of glaucoma. Mol Vis 2007; 13:1783-92.
20. Di Scipio F, Raimondo S, Tos P, Geuna S. A simple protocol for paraffin embedded
myelin sheath staining with osmium tetroxide for light microscope observation. Microsc Res Tech 2008; 71(7): 497-502.
21. Vasudevan, S., Huang, J., Botterman, B., Matloub, H., Keefer, E., and Cheng, J., 2014, Detergent-free Decellularized Nerve Grafts for Long-gap Peripheral Nerve Reconstruction, Plast Reconstr Surg Glob Open. August; 2(8): e201

Although the presently disclosed subject matter and its advantages have been described in detail, it should be understood that various changes, substitutions and alterations can be made herein without departing from the spirit and scope of the disclosed subject matter as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

From the foregoing description, various modifications and changes in the compositions and methods will occur to those skilled in the art. All such modifications coming within the scope of the appended claims are intended to be included therein.

Patents, patent applications, publications, product descriptions, and protocols are cited throughout this application the disclosures of which are incorporated herein by reference in their entireties for all purposes.

What is claimed is:

1. A composite nerve guide for reconstruction of a nerve defect comprising:
   a. an outer nerve conduit, wherein the outer nerve conduit comprises a biodegradable polymer tube having a lumen comprising an inner layer that includes a biodegradable polymer, into which are embedded double-walled microspheres; and an outer layer comprising a biodegradable polymer, wherein said outer layer encapsulates the inner layer; and
   b. an inner nerve graft, wherein a length of the inner nerve graft is longer than the outer nerve conduit, wherein the outer nerve conduit surrounds a middle portion of the inner nerve graft, and wherein both proximal and distal ends of the inner nerve graft are located outside of the lumen.

2. The composite nerve guide of claim 1, the biodegradable polymer is selected from the group consisting of poly(caprolactone), poly(lactic-co-glycolic acid), poly(lactide), and a combination thereof.

3. The composite nerve guide of claim 1, wherein a poly(lactic-co-glycolic acid) layer forms a core and a poly(lactide) layer forms a shell of the double-walled microsphere.

4. The composite nerve guide of claim 1, wherein the double-walled microspheres include an active agent.

5. The composite nerve guide of claim 4, wherein the active agent is a neurotrophic factor.

6. The composite nerve guide of claim 5, wherein the neurotrophic factor is selected from the group consisting of a glial cell-line derived neurotrophic factor (GDNF), a glial growth factor 2 (GGF2), and a combination thereof.

7. The composite nerve guide of claim 4, wherein the double-walled microspheres provide sustained release of the active agent over at least seven days in an amount effective in promoting nerve regeneration.

8. The composite nerve guide of claim 1, wherein the inner nerve graft is selected from the group consisting of a nerve allograft, a nerve autograft, a nerve xenograft, and a combination thereof.

9. The composite nerve guide of claim 1, wherein the inner nerve graft is an acellular nerve graft.

10. The composite nerve guide of claim 9, wherein the acellular nerve graft is decellularized by a treatment, wherein the treatment comprises-gamma irradiation, mechanical decellularization, detergent-processing, or combinations thereof.

11. The composite nerve guide of claim 1, wherein the nerve defect is greater than about 3 cm.

12. A method of promoting nerve generation comprising implanting a composite nerve guide including: (a) an outer nerve conduit, wherein the outer nerve conduit comprises a biodegradable polymer tube having a lumen comprising an inner layer that includes a biodegradable polymer, into which are embedded double-walled microspheres; and an outer layer comprising a biodegradable polymer, wherein said outer layer encapsulates the inner layer; and (b) an inner nerve graft, wherein a length of the inner nerve graft is longer than the outer nerve conduit, wherein the outer nerve conduit surrounds a middle portion of the inner nerve graft, and both proximal and distal ends of the inner nerve graft are located outside of the lumen.

13. The method of promoting nerve generation of claim 12, the biodegradable polymer is selected from the group consisting of poly(caprolactone), poly(lactic-co-glycolic acid), poly(lactide), and a combination thereof.

14. The method of promoting nerve generation of claim 12, wherein a poly(lactic-co-glycolic acid) layer forms a core and a poly(lactide) layer forms a shell of the double-walled microsphere.

15. The method of promoting nerve generation of claim 12, wherein the double-walled microspheres include an active agent.

16. The method of promoting nerve generation of claim 15, wherein the active agent is a neurotrophic factor.

17. The method of promoting nerve generation of claim 16, wherein the neurotrophic factor is selected from the group consisting of a glial cell-line derived neurotrophic factor (GDNF), a glial growth factor 2 (GGF2), and a combination thereof.

18. The method of promoting nerve generation of claim 15, wherein the double-walled microsphere provide sustained release of the active agent over at least seven days in an amount effective in promoting nerve regeneration.

19. The method of promoting nerve generation of claim 12, wherein the inner nerve graft is selected from the group consisting of a nerve allograft, a nerve autograft, a nerve xenograft, and a combination thereof.

20. The method of promoting nerve generation of claim 12, wherein the inner nerve graft is an acellular nerve graft.

21. The method of promoting nerve generation of claim 20, wherein the acellular nerve graft is decellularized by a treatment, wherein the treatment comprises gamma irradiation, mechanical decellularization, detergent-processing, or combinations thereof.

22. The method of promoting nerve generation of claim 12, wherein the composite guide is implanted into a nerve defect greater than about 3 cm.

* * * * *

UNITED STATES PATENT AND TRADEMARK OFFICE
CERTIFICATE OF CORRECTION

| | | |
|---|---|---|
| PATENT NO. | : 11,623,022 B2 | Page 1 of 1 |
| APPLICATION NO. | : 16/763753 | |
| DATED | : April 11, 2023 | |
| INVENTOR(S) | : Kacey Gribbin Marra et al. | |

It is certified that error appears in the above-identified patent and that said Letters Patent is hereby corrected as shown below:

In the Specification

Please correct the paragraph in Column 1, Lines 17-20 as follows:
-- This invention was made with government support under grants W81-XWH-08-2-0032 and W81-XWH-14-2-0003 awarded by the Department of Defense. The government has certain rights in the invention --

Signed and Sealed this
Eighteenth Day of March, 2025

Coke Morgan Stewart
*Acting Director of the United States Patent and Trademark Office*